United States Patent [19]

Beylin et al.

[11] Patent Number: 5,481,000
[45] Date of Patent: Jan. 2, 1996

[54] PROCESS FOR PREPARING CHIRAL [[(2-BROMOETHYL)-AMINO]METHYL]-2-NITRO-1H-IMIDAZOL-1-ETHANOL AND RELATED COMPOUNDS

[75] Inventors: Vladimir G. Beylin; Anthony D. Sercel; Howard D. H. Showalter, all of Ann Arbor, Mich.; Gerald E. Adams, Wheatley, England; Edward M. Fielden, Blewbury, England; Matthew A. Naylor, Woking, England; Ian J. Stratford, Faringdon, England

[73] Assignee: Warner-Lambert Company, Morris Plains, N.J.

[21] Appl. No.: 359,226

[22] Filed: Dec. 19, 1994

Related U.S. Application Data

[62] Division of Ser. No. 245,718, May 18, 1994, abandoned, which is a division of Ser. No. 102,658, Aug. 5, 1993, Pat. No. 5,342,959, which is a continuation of Ser. No. 923,209, Jul. 31, 1992, abandoned.

[51] Int. Cl.$^6$ ............................................. C07D 233/64
[52] U.S. Cl. ............................................. 548/229
[58] Field of Search ............................................. 548/229

[56] References Cited

U.S. PATENT DOCUMENTS

| | | | |
|---|---|---|---|
| 4,241,060 | 12/1980 | Smithen | 424/248.57 |
| 4,282,232 | 8/1981 | Agrawal | 424/267 |
| 4,581,368 | 4/1986 | Ahmed et al. | 514/397 |
| 4,596,817 | 6/1986 | Ahmed et al. | 514/397 |
| 4,631,289 | 12/1986 | Ahmed et al. | 514/397 |
| 4,757,148 | 7/1988 | Ahmed et al. | 548/338 |
| 4,954,515 | 9/1990 | Suto | 514/398 |
| 5,098,921 | 3/1992 | Adams et al. | 514/383 |
| 5,342,959 | 8/1994 | Beylin et al. | 548/327.5 |

FOREIGN PATENT DOCUMENTS

| | | | |
|---|---|---|---|
| 0095906 | 12/1983 | European Pat. Off. | 548/327.5 |
| 0319329 | 6/1989 | European Pat. Off. | 548/327.5 |
| 0375951 | 7/1990 | European Pat. Off. | 548/327.5 |

OTHER PUBLICATIONS

CA111:214488z Nitro–substituted . . . compositions. Adams et al., 1989.
Acta Crystallographica, vol. C46, Walton et al., pp. 614–617, 1990.
Organic Chemistry, 2nd ed., Karrer, pp. 93–97, 1946.
J. Med. Chem. Synthesis . . . Cytotoxins, Jenkins et al., vol. 33, pp. 2603–2610, 1990.
CA113:171945t Synthesis . . . Cytotoxins. Jenkins et al., p. 699, 1990.
CA114:42787q Preparation . . . Chemotherapy. Suto, p. 746, 1991.

*Primary Examiner*—Joseph K. McKane
*Attorney, Agent, or Firm*—Charles W. Ashbrook; Todd M. Crissey

[57] ABSTRACT

Chiral compounds useful as radiosensitizers or chemosensitizers having the formula

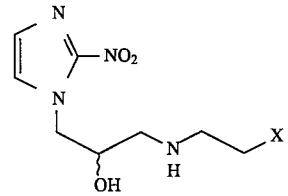

wherein X is halogen o

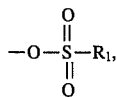

intermediates used to prepare these compounds, and a novel process to prepare these compounds are described.

1 Claim, No Drawings

PROCESS FOR PREPARING CHIRAL [[ (2-BROMOETHYL)-AMINO] METHYL] -2-NITRO-1H-IMIDAZOL-1-ETHANOL AND RELATED COMPOUNDS

This is a divisional of U.S. application Ser. No. 08/245,718 filed May 18, 1994, now abandoned, which is a divisional of U.S. application Ser. No. 08/102,658 filed Aug. 5, 1993, now U.S. Pat. No. 5,342,959 issued Aug. 30, 1994, which is a continuation of U.S. application Ser. No. 07/923,209 filed Jul. 31, 1992, now abandoned.

FIELD OF INVENTION

This invention relates to a novel method for preparing the enantiomeric forms of certain known racemic imidazole-1-ethanol derivatives which are useful as radiosensitizing or chemosensitizing agents. Novel intermediates utilized in this process are also involved as well as the chiral final products.

BACKGROUND OF INVENTION

The racemic mixture of certain compounds of the present invention is described in U.S. Patent 4,954,515 and 5,098,921. In particular, Example 2 of both patents describes the racemic mixture of the compound of Formula I set forth below wherein X is bromo. The racemic mixture of certain compounds of the present invention is also described generically as starting materials or intermediates in the following U.S. Pat. Nos. 4,596,817; 4,631,289; 4,757,148. Additionally, the racemic mixture of certain compounds of Formula I is described generically in U.S. Pat. No. 4,241,060 as hypoxic-cell radiosensitizers.

SUMMARY OF INVENTION

The present invention provides a novel process for the preparation of the enantiomers of compounds of the following general formula:

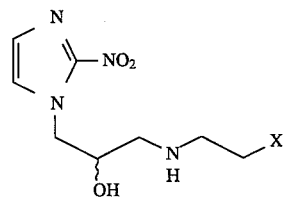

Formula I wherein X is halogen o

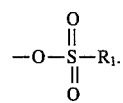

In Formula I, X can be chlorine, bromine, fluorine, or iodine and preferably X is bromine or chlorine, and more preferably X is bromine, and $R_1$ can be OH, methyl, phenyl, or phenyl substituted as defined herein for R.

The present invention also provides novel intermediates useful in the preparation of the enantiomers of the compounds of Formula I. These novel intermediates have the following structures:

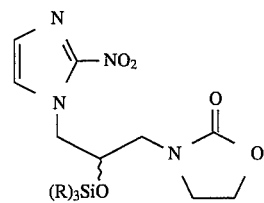

II

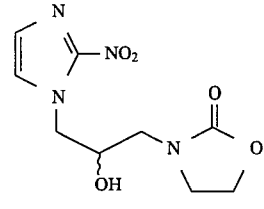

III

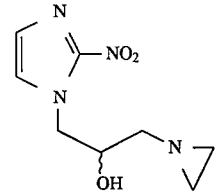

IV

The compound depicted as Formula II above is 3-[3-(2-nitro-1H-imidazol-1-yl)-2-[(tri-R-silyl)oxy]propyl]-2-oxazolidinone. Formula III is 3-[2-hydroxy-3-(2-nitro-1H-imidazol-1-yl)propyl]-2-oxazolidinone; and Formula IV is (1-aziridinylmethyl)-2-nitro-1H-imidazole-1-ethanol. Preferably, R in Compound II is methyl.

The compounds of Formula I and each of the compounds of Formulas II, III, and IV exist in the (R)-(+) or (S)-(–) enantiomeric form or in the (R)-(–) or (S)-(+) enantiomeric form. The most preferred compound of the present invention is the (R)-(+) enantiomer of Formula I wherein X is bromo and this compound is depicted as follows:

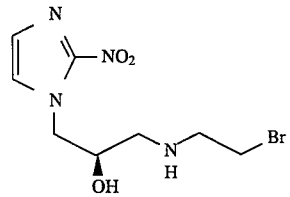

V

Pharmaceutically acceptable salts of the compound of Formula I are also within the present invention. These include salts of inorganic and organic acids, preferably inorganic acids such as hydrochloric, hydrobromic, and hydriodic acid. Most preferred of the salts is the hydrobromide.

The preferred enantiomer for the compound of Formula II where R is methyl is the (S)-(+) enantiomer; for the compound of Formula III is the (S)-(–) enantiomer, and for the compound of Formula IV is the (R)-(–) enantiomer.

The novel process of the present invention comprises reacting chiral 2-nitro-1-(2-oxiranylmethyl)-1H-imidazole with a 2-oxazolidinone of the formula

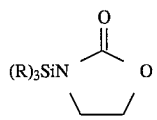

wherein R is a lower alkyl group having from 1 to 4 carbon atoms, phenyl or phenyl substituted with lower alkyl having from 1 to 4 carbon atoms, lower alkoxy having from 1 to 4 carbon atoms, hydroxy, halogen such as chlorine, bromine, or fluorine, nitro, amino, or trifluoromethyl in the presence of a suitable catalyst to give a chiral compound of the formula

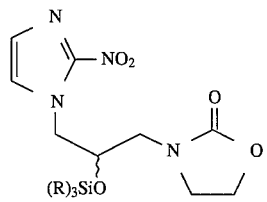

wherein R has the meaning defined above which is (a) hydrolyzed, for example, with potassium fluoride in methanol or acetic acid in methanol to give chiral 3-[2-hydroxy-3-(2-nitro-1H-imidazol-1-yl)propyl]-2-oxazolidinone which is treated with an appropriate acid of formula HX wherein X is as defined above, preferably in acetic acid; the preferred acid being hydrobromic acid; or (b) treated in one step with such an acid to give a compound of Formula I.

DETAILED DESCRIPTION OF INVENTION

The compounds of Formula I are prepared as depicted in Chart I hereof. Although the preferred reagents and solvents are depicted in each of the steps, it is readily apparent that the reaction conditions may be varied somewhat. For example, in Step 1, suitable solvents include epichlorohydrin alone, lower aliphatic alcohols, water, ethers such as diethyl ether, and diisopropyl ether or tetrahydrofuran, and lower dialkyl ketones such as acetone. Typical bases that can be used include essentially all metal carbonates, especially those of Group I metals (Na, K, Rb, Cs), also common amine bases such as the tertiary lower alkyl amines (triethylamine, diisopropyl ethylamine, N—Me—pyrrolidine, etc). Also common metal hydrides such as NaH. Quaternary ammonium bases such as $nBu_4N^+OH^-$, $nBu_4N^+Cl^-$, etc; various fluoride bases such as $nBu_4NF$, KF, CsF, etc. The temperature of the reaction in Step 1 can vary from room temperature to about 150° C.

In Step 2 of Chart I typical solvents which can be employed include various ethers, lower alcohols; other chlorinated solvents, aromatic hydrocarbons such as benzene, toluene; dipolar aprotic solvents such as DMF, lower dialkyl ketones, lower alkyl nitriles. In Step 2 the temperature can vary from −50° C. to 50° C. and the bases used can be the same as in Step 1.

In Step 3 of Chart I, in addition to using 3-tri-R-silyl-2-oxazolidinone neat as the solvent, other solvents which can be employed include various ethers, chlorinated hydrocarbons, dipolar aprotic solvents such as DMF, lower alkyl nitriles such as acetonitrile, aromatic hydrocarbons, and lower dialkyl ketones such as acetone. In addition to potassium silanolate, other catalysts which can be employed include other-metal silanolates, metal alkoxides, various metal and quaternary ammonium fluorides such as KF, CsF, $nBu_4N^+F^-$, etc. The temperature can vary from 0° C. to 250° C. and the preferred oxazolidinone is 3-trimethylsilyl-2-oxazolidinone. The use of potassium trimethylsilanolate and 3-tri-R-silyl-2-oxazolidinone is a particularly novel feature of the present process.

In Step 4 of Chart I suitable solvents include water, lower alcohols, ethers, and lower alkyl organic acids such as acetic acid and the temperature can vary from 0° C. to 120° C. Suitable catalysts include mineral acids, strong organic acids such as trifluoroacetic acid, and those noted as suitable for Step 3.

In each of Steps 5 and 6 of Chart I, suitable solvents include lower alkyl organic acids and lower alkyl alcohols and acids can be mineral acids but preferably hydrobromic acid.

Chart I also depicts Steps 7 and 8 which represent an alternative method to prepare the chiral compound of Formula I. The oxirane intermediate from Step 2 is reacted with aziridine in an alcoholic solvent. The resulting chiral aziridine intermediate is ring opened with mineral acid in an organic solvent, preferably by hydrobromic acid in acetone.

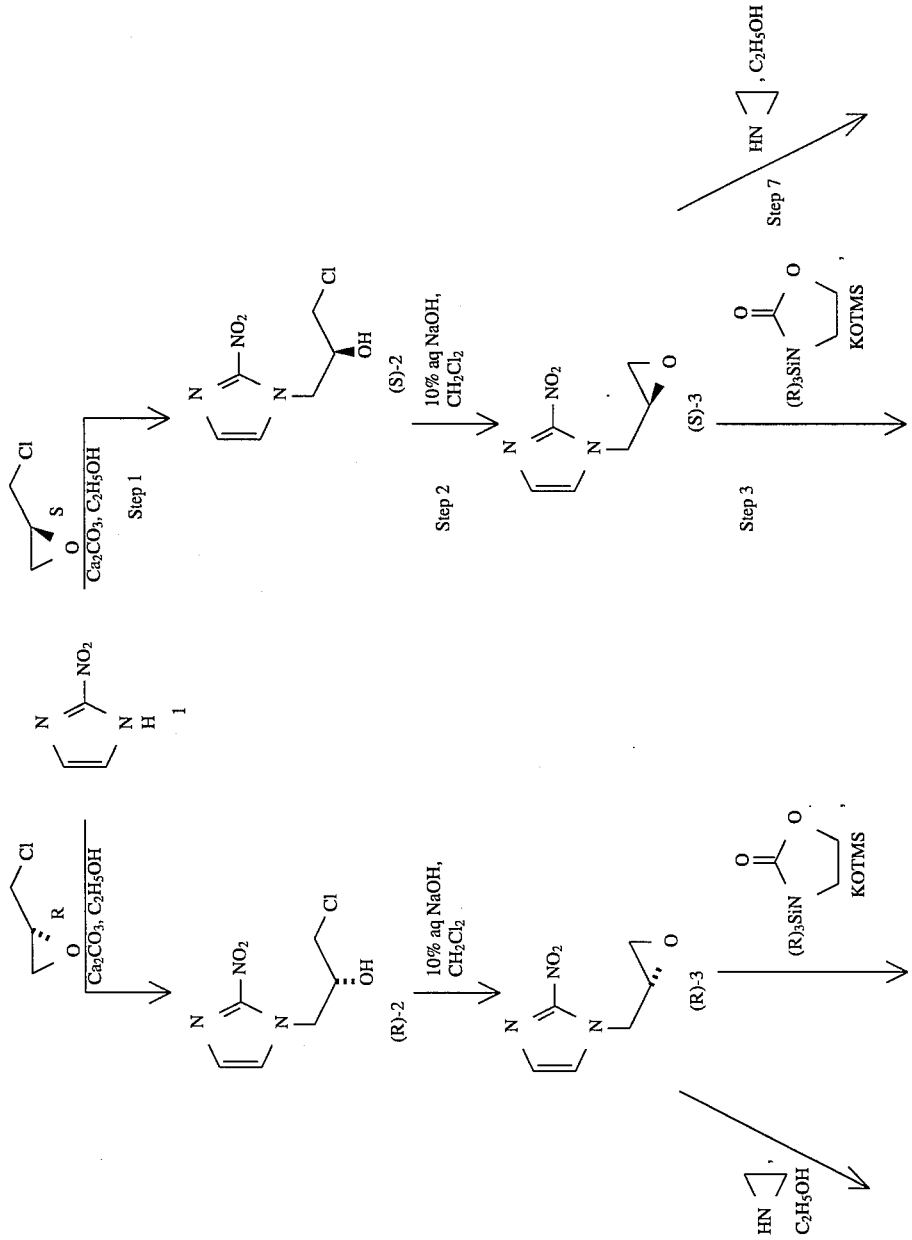

-continued
CHART I
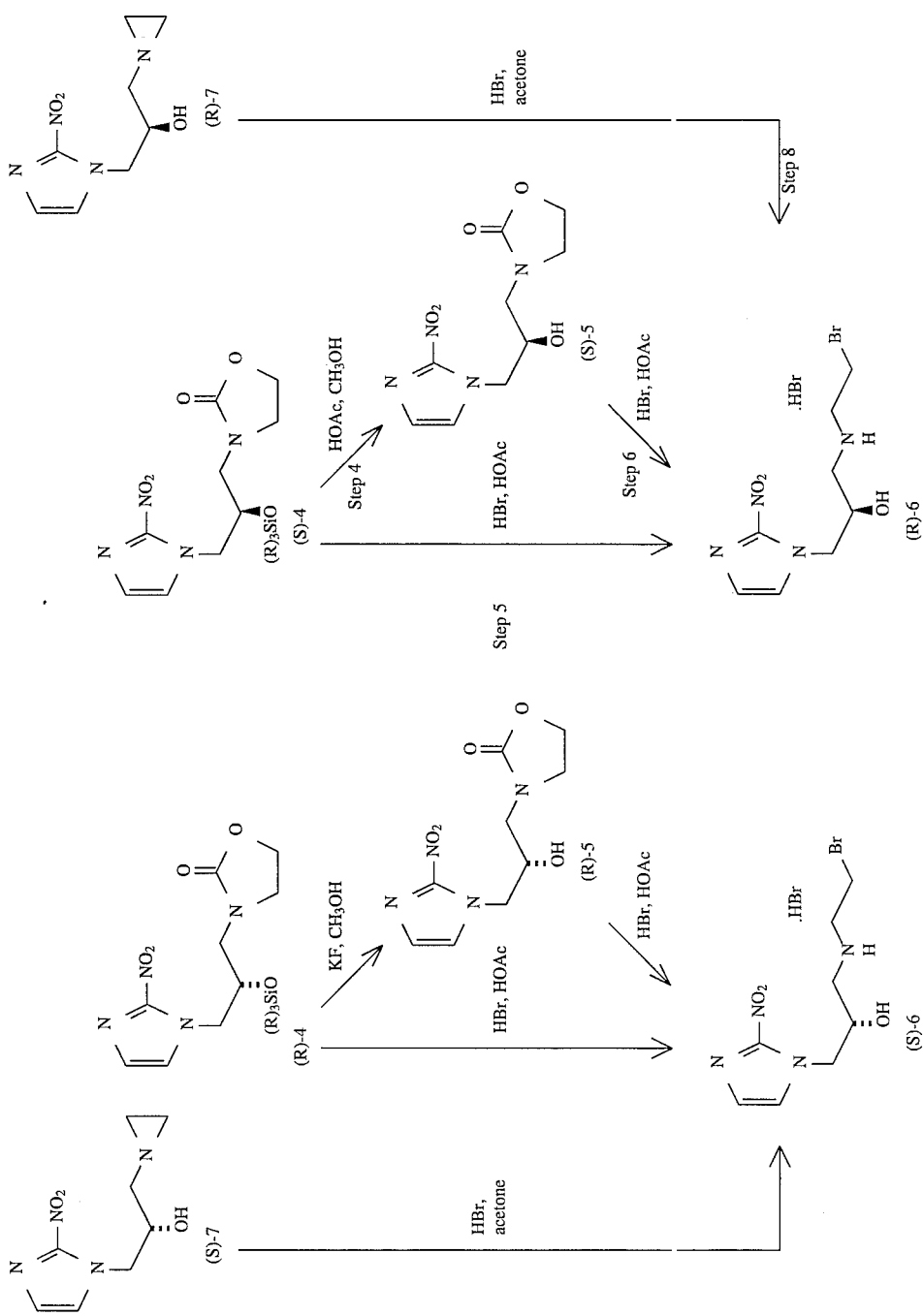

$(R)_3Si$=tri-R-silyl, preferably trimethylsilyl

The novel chiral compounds of Formula I are useful as chemosensitizers or radiosensitizers in patients having cancer. Thus, the compounds of Formula I have utility in patients having cancer which is sensitive to radiation or chemotherapy and are typically administered to said patients prior to being subjected to irradiation of the cancer or being administered chemotherapy. The manner of formulating the compounds of Formula I and the dosage amount of compound to be employed is as described in U.S. Pat. Nos. 5,098,921, 4,954,515 and 4,241,060, and in particular, column 5, line 36 to column 6, line 35 of U.S. Pat. No. 4,241,060, which portion is incorporated herein by reference.

It has been found that the (R)-enantiomer of the compounds of Formula I are particularly useful in that they are substantially devoid of emetic side effects. To illustrate this particular unique utility of the (R)-enantiomers, studies were carried out in beagle dogs on the (R)-enantiomer of a compound of Formula I where X is bromine as follows.

EMESIS STUDIES

Beagle dogs (approximately 10 kg body weight) were treated intravenously with a 10-minute infusion of 20 mL of the test compound prepared in sodium lactate buffer, pH 4.0. Dogs were scored over a 6-hour postdosing period for both the number of emetic episodes and the relative volume. Antiemetic therapy consisted of a 5-minute infusion of ondansetron, administered at a dose of 0.3 mg/kg 30 minutes prior to treatment with the nitroimidazole. The $ED_{50}$ value (expressed in mg/kg) is equivalent to the threshold dose at which 50% of the animals exhibited an emetic response.

MOUSE TOXICITY STUDIES $B_6C_3F_1$ mice were treated with varying doses of test agent by either intraperitoneal, intravenous, or oral administration. Mice were observed for 14 days, noting clinical signs of toxicity and lethality. The maximum tolerated dose was established as the dose equal to or less than the $LD_{10}$ as determined from a probit analysis.

RADIOSENSITIZING EFFICACY IN MICE

Clonogenic survival of KHT fibrosarcomas was determined in assays employing $B_6C_3F_1$ mice. Tumors were implanted subcutaneously by trocar. Nine days postimplantation, when tumors ranged from 200 to 400 mg in size, mice were treated IP with a range of drug doses including the maximum tolerated dose of the test agent. Thirty minutes later mice received whole body irradiation at a dose of 10 Gray, delivered at a rate of 2 Gray/minute with a 320 kV x-ray machine. Twenty-four hours after treatment, animals were sacrificed, and tumors were excised. Tumors were enzymatically digested to give single cell suspensions prior to plating for cell survival by clonogenic assay.

Tumor growth delay was assessed in $B_6C_3F_1$ mice implanted IM with $5 \times 10^5$ SCC7 carcinoma tumor cells. On Days 10 through 13 post tumor implantation, mice were treated every 12 hours with the maximum tolerated dose of test agent (determined from a 10-day multiple treatment schedule). Thirty minutes later, mice were irradiated at the tumor site with a 2.5 Gray dose of x-rays. Upon completion of this 8 fraction protocol, tumor growth was monitored daily.

Results of the above tests on the racemic mixture, the (S) and the (R) isomers are shown in the following table. Although the activity and toxicity of the chiral compounds are comparable to the racemic mixture, the (R) isomer surprisingly shows significantly less emesis than the (S) isomer or the mixture.

| Comparison of Formula I Isomers | | (R/S) | (S) | (R) |
|---|---|---|---|---|
| Toxicity | | | | |
| $LD_{10}$ (mg/kg) | IP | 540 | 850 | 850 |
| | IV | ND | 900 | 900 |
| | PO | 1000 | 1100 | 1100 |
| Efficacy | | | | |
| Excision (250 mg/kg)[a] (% control) | IP | 14 | 11 | 11 |
| Growth Delay[b] Fold Enhancement | IP | 1.8 | 1.8 | 2.1 |
| Emesis (Dogs) | | | | |
| $ED_{50}$ (mg/kg) | IV | ~8 (6–12) | 4 | 12 |

[a]KHT fibrosarcoma
[b]SCC7 carcinoma

The following illustrate in more detail the preparation of the chiral compounds of Formula I where X is bromine.

EXAMPLE 1

(S)-(−)-5-[[(2-Bromoethyl)amino]methyl]-2-nitro-1H-imidazole-1-ethanol, monohydrobromide (a)

(R)-(−)-α-(Chloromethyl)-2-nitro-1H-imidazole-1-ethanol

A stirred suspension of 63.4 g (561 mmole) of 2-nitroimidazole, 9.1 g (28.1 mole) of anhydrous cesium carbonate, and 1.1 L of absolute ethanol maintained under nitrogen at room temperature is treated with 57 mL (729 mole) of (R)-(−)-epichlorohydrin. The mixture is heated to gentle reflux for 2 hours. The hot solution is filtered through a preheated pad of ethanol-moistened Celite®, the pad is washed with a little ethanol, and the filtrate is diluted with 170 mL of hexane. The filtrate is cooled at 0°–5° C. for 1 day. The resultant crystals are collected by filtration, washed with 120 mL ethyl acetate: diethyl ether (1:1), and dried to give 46.7 g of product as tan needles, mp 126.5°–128° C., 93.9% pure by HPLC.

The mother liquor is concentrated to a solid residue that is suspended in 500 mL of ethyl acetate. The suspension is heated to boiling then filtered hot through preheated moist Celite. The filtrate is maintained at room temperature for 3 hours, then at 0°–5° C. for 35 hours. The resultant crystals are collected by filtration as above to give 31.9 g of a second crop, mp 127°–128.5° C., 97.4% pure by HPLC.

The mother liquor is further processed as above to give 9.2 g of a third crop of less pure product, mp 124°–127° C.

A 1.5-g sample of second crop product is dissolved in 30 mL of boiling ethyl acetate. The solution is treated with charcoal, filtered hot, then maintained first at room temperature for 16 hours then at 0°–5° C. for 48 hours. The resultant crystals are processed as above to give 0.49 g of product as light yellow plates, mp 128°–129° C.; $[\alpha]_D^{25}$=−2.57° [cl, methanol].

Alternatively, a mixture of 0.42 g (3.7 mmole) of 2-nitroimidazole, 85 mg (0.62 mole) of anhydrous potassium carbonate, and 5 mL of (R)-(−)-epichlorohydrin is refluxed for 10 minutes then filtered while hot. The filtrate is concentrated and cooled to give a solid. Crystallization from ethanol and further processing as above gives 0.56 g of the product.

(b)
(R)-(+)-2-Nitro-1-(2-oxiranylmethyl)-1H-imidazole

Reaction of 40.2 g (196 mole) of (R)-(−)-α-(chloromethyl)-1H-imidazole, 400 mL of 10% aqueous sodium hydroxide, and 400 mL of dichloromethane as described in Example 2 (b) below gives 29.6 g of product, mp 42°–44° C. Purification of a 1.35-g portion of product as described in Example 2(b) below gives 822 mg of product, mp 43°–44° C., 99.9% pure by HPLC; $[\alpha]_D^{25}=+84.95°$ [cl, methanol].

Alternatively, reaction of (R)-(−)-α-(chloromethyl)-1H-imidazole with 10% aqueous sodium hydroxide as described in Example 2(b) below gives the product.

(c) (R)-3-[3-(2-Nitro-1H-imidazol-1-yl)-2-[(trimethylsilyl)oxypropyl]-2-oxazolidinone Reaction of 8.46 g (50 mole) of (R)-(+)- 2-nitro-1-(2-oxiranylmethyl)-1H-imidazole, 9.4 mL (59.8 mmole) of 3-trimethylsilyl-2-oxazolidinone, and 64 mg of potassium trimethylsilanolate followed by workup as described in Example 2(c) below gives 8.04 g of pure product, mp 98°–100° C.; $[\alpha]_D^{25}-14.54°$ [cl, methanol].

(d) (R)-3-[2-Hydroxy-3-(2-nitro-1H-imidazol-1-yl)propyl]-2-oxazolidinone

Reaction of 493 mg of (R)-3-[3-(2-nitro- 1H-imidazol-1-yl )-2-[(trimethylsilyl)oxy]propyl]-2-oxazolidinone with 3 mL of 1:1 methanol:glacial acetic acid as described in Example 2(d) below gives 40 mg of product, mp 136°–137° C., 98% pure by HPLC; $[\alpha]_D^{25}=+5.80°$ [cl, methanol].

(e)
(S)-(+)-α-(1-Aziridinylmethyl)-2-nitro-1H-imidazole-1-ethanol

A solution of 0.3 g (1.8 mole) of (R)-(+)- 2-nitro-1-(2-oxiranylmethyl)-1H-imidazole, 0.24 g (5.4 mmole) of 1H-aziridine, and 3.5 mL of 99:1 absolute ethanol:triethylamine is heated at reflux for 10 minutes, cooled, and concentrated. The residue is crystallized from 99:1 absolute ethanol:triethylamine to give 0.22 g of product, mp 118.5°–120° C. $[\alpha]_D^{24}=+23.5°$ [C0.98, chloroform].

(f)
(S)-(−)-α-[[(2-Bromoethyl)amino]methyl]-2-nitro-1H-imidazole-1-ethanol, monohydrobromide A mixture of 257 mg (1 mole) of (R)-3-[ 2-hydroxy-3-(2-nitro-1H-imidazol-1-yl )propyl]-2-oxazolidinone and 1 mL of 31% hydrogen bromide in acetic acid is stirred at room temperature for 7 days. The precipitated solids are collected by filtration, washed successively with 10 mL of 2:1 diethyl ether:2-propanol then 10 mL of diethyl ether, and air dried to leave 385 mg of product. The product is dissolved in 2 mL of hot methanol and the solution is stored at 25° C. for 3 hours, then at 0°–5° C. for 19 hours. The solids are collected by filtration, washed with 5 mL of 1:1 diethyl ether:ethanol, and dried at 40° C./200 mm/15 hours to give 209 mg of pure product as the monohydrobromide salt, mp 153°–154.5° C. (decomposition), 99.3% pure by HPLC.

Alternatively, reaction of 28.11 g (85.6 mmole) of (R)-3-[3-(2-nitro-1H-imidazol-1 -yl)- 2[(trimethylsilyl)oxy]propyl]2-oxazolidinone, synthesized as described in Example 1(c), with 142 mL of 31% hydrogen bromide in acetic acid at room temperature for 4 days followed by workup as described in Example 2(f) below gives 18.12 g of pure product as the monohydrobromide salt, mp 154°–155.5° C. (decomposition), 100% optically pure by chiral HPLC; $[\alpha]_D^{25}=-6.94°$ (cl, methanol)

In another alternate procedure, treatment of S-(+)-α-(1-aziridinylmethyl)-2-nitro-1H-imidazole-1-ethanol, synthesized as described in Example 1(e), with aqueous hydrogen bromide in acetone, as described in *The journal of Medicinal Chemistry* 33, 2608 (1990) gives the product, mp 148°–149° C. (decomposition), 97.1% optically pure by chiral HPLC.

EXAMPLE 2

R-(+)-α-[[(2-Bromoethyl)amino]methyl]-2-nitro-1H-imidazole-1-ethanol, monohydrobromide (a)
(S)-(+)-α-(Chloromethyl)-2-nitro-1H-imidazole-1-ethanol Reaction of a mixture of 75.6 g (669 mmole) of 2-nitroimidazole, 68 mL (869 mmole) of (S)-(+)-epichlorohydrin, 10.9 g (33.5 mmole) of anhydrous cesium carbonate, and 1.3 L of absolute ethanol as described in Example 1 gives 101.5 g of product, 92.6% pure by HPLC. A 9.87 g sample is recrystallized from 195 mL of ethyl acetate to give 7.45 g of pure product, mp 128°–129° C.; $[\alpha]_D^{25}=+2.39°$ [cl, methanol].

Alternatively, reaction of 2-nitroimidazole, anhydrous potassium carbonate, and (S)-(+)-epichlorohydrin as described in Example 1(a) gives the product.

(b)
(S)-(−)-2-Nitro-1-(2-oxiranylmethyl)-1H-imidazole

To a vigorously stirring ice-cold suspension of 100.5 g (489 mmole) of (S)-(+)-α-(chloromethyl)-2-nitro-1H-imidazole-1-ethanol in 1 L of dichloromethane is added over 1 minute 1 L of 10% aqueous sodium hydroxide. The biphasic mixture is stirred for 7.5 hours at 0°–5° C., then diluted with 500 mL each of chloroform and water. The phases are separated and the aqueous phase is extracted three times with 200 mL portions of chloroform. The combined organic phases are dried over magnesium sulfate and concentrated to leave 71.1 g of a yellow oil that crystallizes upon prolonged storage at 0°–5° C. The crystals are dried at 0.05 m/25° C./8 hours to give 69.1 g of product, mp 42°–43° C., 98.4% pure by HPLC.

A portion (1.14 g) of the product is dissolved in 20 mL of ethyl acetate and the solution is loaded onto a silica gel (230–400 mesh) column (4×13 cm). The column is eluted with 1:1 ethyl acetate: cyclohexane. Pure product fractions are combined and evaporated to a solid that is crystallized from 14 mL of 5.2 hexane:ethyl acetate. The solution is kept at −5° to 0° C. for 6 hours and the solids are collected by filtration, washed with 20 mL of diethyl ether, and dried at 0.025 m/25° C. to give 681 mg of product as pale yellow crystals, mp 43°–44° C., 99% pure by HPLC; $[\alpha]_D^{25}=-$ 82.18° [cl, methanol].

Alternatively, reaction of 0.56 g of (S)-(+)-α-(chloromethyl)-2-nitro-1H-imidazole-1-ethanol with 3 mL of 10% aqueous sodium hydroxide at 25° C. for 30 minutes followed by further processing as above gives 0.3 g of the product.

(c) (S)-3-[3-(2-Nitro-1H-imidazol-1-yl)-2-[(trimethylsiyl)oxy]propyl]-2-oxazolidinone Under a brisk stream of dry nitrogen, a vigorously stirring mixture of 40.3 mL (256 mole) of 3-trimethylsilyl-2-oxazolidinone and 274 mg (2.1 mole) of potassium trimethylsilanolate is heated to 95° C. To the solution is added over 10 minutes a solution of 36.15 g (214 mole) of (S)-(−)-2-nitro-1-(2-oxiranylmethyl)-1H-imidazole in 26 mL of dry tetrahydrofuran during which an opening in the flask allows evaporation of solvent. The addition funnel is rinsed with 5 mL of solvent, and the flask is kept open for an additional 15 minutes. After heating at 95° C. for a total of 1.5 hours, 3.4 mL of additional 3-trimethylsilyl-2-oxazolidinone is added to the solution. The mixture is heated for an additional 1.5 hours then concentrated at 0.8 mm/50° C./16 hours to give an oil that is dissolved in 100 mL of 2:1 ethyl acetate:cyclohexane. The solution is loaded onto a column containing an 8×16 cm pad of silica gel (230–400 mesh). The column is eluted with ~5 L of 2:1 ethyl acetate: cyclohexane. Product fractions are combined and concentrated first at 20 ram, then at 0.8 mm to give 71.45 g of an oil that solidifies on standing. The solids are diluted with 200 mL of tert-butyl methyl ether, and the suspension is refluxed for 45 minutes, cooled, and filtered. The solids are washed sparingly with tert-butyl methyl ether and dried to leave 37.18 g of pure product as a light yellow solid, mp 98°–100° C.; $[\alpha]_D^{25}=+15.4°$ [cl, methanol].

The tert-butyl methyl ether filtrate is concentrated to leave ~30 g of a viscous oil that is dissolved in 100 mL of 1:1 ethyl acetate:cyclohexane. The solution is loaded onto an 8×16 cm pad of silica gel as above and the column is eluted with 1:1 ethyl acetate: cyclohexane until pure product appears. The column is then eluted with ~3 L of 2:1 ethyl acetate: cyclohexane. Pure product fractions are combined and concentrated as above to leave 13 g of a sticky solid that is triturated in 1:1 diethyl ether:ethyl acetate to leave 5.67 g of a second crop, mp 95°–98° C., after drying.

(d) (S)-3-[2-Hydroxy-3-(2-nitro-1H-imidazol-1-yl)propyl]-2-oxazolidinone

A solution of 10.51 g (32 mole) of (S)-3-[3-(2-nitro-1H-imidazol-1-yl)-2-[(trimethylsilyl)oxy] propyl]-2-oxazolidinone and 32 mL of 1:1 methanol:glacial acetic acid is stirred at 25° C. for 16 hours during which a precipitate forms. The suspension is diluted with 30 mL of absolute ethanol, and the solids are collected by filtration, washed with ethanol and dried to give 6.49 g of a pure white solid, mp 134°–136° C., 98.5 % optically pure by chiral HPCL; $[\alpha]_D^{25}=-5.97°$ [cl, methanol].

The filtrate is concentrated to near dryness and the solids are dissolved in methanol. The solution is decolorized with charcoal, then filtered through a pad of silica gel (230–400 mesh). The filtrate volume is reduced to 20 mL and the solution is refrigerated overnight. The solids are collected by filtration, then dissolved in ~10 mL of methanol. The solution is refrigerated for 3 hours and the solids are collected by filtration, washed with methanol, and dried to leave a second crop as a light yellow solid, mp 134°–136° C. The combined filtrates from the above two crystallizations are concentrated to a solid that is crystallized from methanol as above to give a third crop of product, mp 134°–136° C. The second and third crops are combined and dried to leave 1.18 g of product, 100% optically pure by chiral HPLC; $[\alpha]_D^{25}-5.92$ [cl, methanol].

(e) (R)-(−)-α-(1-Aziridinylmethyl)-2-nitro-1H-imidazole-1-ethanol

Reaction of (S)-(−)-2-nitro-1-(2-oxiranylmethyl)-1H-imidazole with 1H-aziridine as described in Example 1(e) gives the product, mp 119.5°–121° C. $[\alpha]_D^{24}-28.7°$ [cl. 15, chloroform].

(f) (R)-(+)-α-[[(2-Bromoethyl)amino]methyl]-2-nitro-1H-imidazole-1-ethanol, monohydrobromide A mixture of 8.5 g (33.2 mmole) of (S)-3-[2-hydroxy-3-(2-nitro-1H-imidazol-1-yl)propyl]-2-oxazolidinone and 51 mL of 31% hydrogen bromide in acetic acid is stirred at room temperature for days. The precipitated solids are collected by filtration, washed successively with 70 mL of 1 diethyl ether:2-propanol then 100 mL of diethyl ether, and air dried to leave 11.8 g of product, mp 149°–151° C. (decomposition). The product is dissolved in 100 mL of hot methanol, the solution filtered through Celite, and the filtrate stored at 25° C. for 6 hours then at 0°–5° C. for 8 hours. The solids are collected by filtration, washed with 30 mL of 1:1 diethyl ether:methanol, and dried at 55° C./150 mm/15 hours to give 7 g of pure product as the monohydrobromide salt, mp 154°–156° C. (decomposition), 100% optically pure by chiral HPLC; $[\alpha]_D^{25}=+5.57°$ [cl, methanol].

Alternatively, to an ice-cold solution of 160 mL of 31% hydrogen bromide in acetic acid was added 31.2 g (95 mmole) of (S)-3-[3-(2-nitro-1H-imidazol- 1-yl)-2-[(trimethylsilyl)oxy]propyl]-2-oxazolidinone, synthesized as described in Example 2(c), and the solution is allowed to slowly warm to 25° C. then stirred for 23.5 hours. The solids are collected by filtration, washed with 100 mL of 2:1 diethyl ether:2-propanol, and dried to leave 28.85 g of first crop material. The filtrate is poured slowly into a rapidly stirring solution of 1.2 L of 2:1 diethyl ether:2-propanol. The precipitated solids are collected by filtration, washed with ~200 mL of 2:1 diethyl ether:2-propanol, then dissolved in a mixture of 80 mL of 1:1 31% hydrogen bromide in acetic acid: 2-propanol. The solution is stirred at 25° C. for 24 hours and the solids are collected by filtration then processed as above to leave 5.35 g of a second crop. The crops are combined and dissolved in 280 mL of hot methanol. The solution is maintained at 25° C. for 2 hours, then refrigerated for 4 hours. The solids are collected by filtration, washed with methanol, and dried to leave 17.62 g of product as the monohydrobromide salt, mp 157°–159° C. (decomposition), 100% optically pure by chiral HPLC; $[\alpha]_D^{25}=+5.55°$ [cl, methanol].

The filtrate is concentrated to a solid that is crystallized in ~60 mL of methanol as above to leave 3.8 g of second crop material, mp 152°–154° C. (decomposition). Further processing of the filtrate affords 1.5 g of third crop and 0.5 g of fourth crop materials, mp 145°–150° C. (decomposition). The second through fourth crops are combined and crystallized in 60 mL of hot methanol, with cooling at −20° C. for 7 hours, and further processing as above to give 4.59 g of product, 100% optically pure by chiral HPLC; $[\alpha]_D^{25}=+5.71°$ [cl, methanol].

In another alternate procedure, treatment of (R)-(−)-α-(1-aziridinylmethyl)-2-nitro-1H-imidazole-1-ethanol, synthesized as described in Example 2(e), with aqueous hydrogen bromide in acetone, as described in *The Journal of Medicinal Chemistry*, 33, 2608 (1990), gives the product, mp 149°–150.5° C. (decomposition), 99.3% optically pure by chiral HPLC.

We claim:

1. A chiral compound of the formula

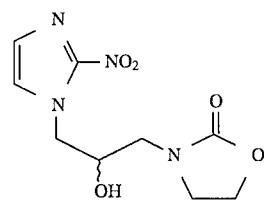

wherein the compound has the (S) configuration at the carbon having the OH substituent and is substantially free of the (R) configuration.

* * * * *